United States Patent
Auguste et al.

(10) Patent No.: US 7,189,388 B2
(45) Date of Patent: *Mar. 13, 2007

(54) MASCARA COMPRISING SOLID PARTICLES

(75) Inventors: Frédéric Auguste, Chevilly-Larue (FR); Florence Tournilhac, Paris (FR)

(73) Assignee: L'Oreal S.A., Paris (FR)

( * ) Notice: Subject to any disclaimer, the term of this patent is extended or adjusted under 35 U.S.C. 154(b) by 59 days.

This patent is subject to a terminal disclaimer.

(21) Appl. No.: 10/195,432

(22) Filed: Jul. 16, 2002

(65) Prior Publication Data

US 2003/0064038 A1 Apr. 3, 2003

Related U.S. Application Data

(60) Provisional application No. 60/306,443, filed on Jul. 20, 2001.

(30) Foreign Application Priority Data

Jul. 16, 2001 (FR) .................................. 01 09504

(51) Int. Cl.
*A61Q 1/10* (2006.01)
*A61Q 5/00* (2006.01)

(52) U.S. Cl. ................. 424/70.7; 424/70.1; 424/70.22; 424/70.13; 424/70.16; 424/401

(58) Field of Classification Search ................ 424/401, 424/707

See application file for complete search history.

(56) References Cited

U.S. PATENT DOCUMENTS

| | | | |
|---|---|---|---|
| 3,937,811 A | | 2/1976 | Papantoniou et al. |
| 5,389,363 A | * | 2/1995 | Snyder et al. ............. 424/70.7 |
| 5,660,818 A | | 8/1997 | Dubief et al. |
| 5,720,943 A | | 2/1998 | Mougin et al. |
| 5,849,278 A | | 12/1998 | Piot et al. |
| 5,851,517 A | | 12/1998 | Mougin et al. |
| 5,858,338 A | | 1/1999 | Piot et al. |
| 5,945,095 A | | 8/1999 | Mougin et al. |
| 5,961,989 A | | 10/1999 | Mougin et al. |
| 6,001,168 A | | 12/1999 | Hall-Goulle et al. |
| 6,254,877 B1 | | 7/2001 | De La Poterie et al. |
| 6,264,933 B1 | | 7/2001 | Bodelin et al. |
| 6,274,131 B1 | | 8/2001 | Piot et al. |
| 6,372,201 B1 | | 4/2002 | Leuridan et al. |
| 6,491,931 B1 | * | 12/2002 | Collin ........................ 424/401 |
| 6,682,748 B1 | * | 1/2004 | De La Poterie et al. .... 424/401 |
| 2001/0006665 A1 | | 7/2001 | Auguste |
| 2002/0085986 A1 | | 7/2002 | De La Poterie et al. |
| 2004/0009201 A1 | | 1/2004 | Collin et al. |

FOREIGN PATENT DOCUMENTS

| | | |
|---|---|---|
| FR | 2 756 731 | 6/1998 |
| JP | H04-210613 | 7/1992 |
| JP | 06-9341 | 1/1994 |
| JP | H07-291826 | 11/1995 |
| JP | H07-304639 | 11/1995 |
| JP | H09-2920 | 1/1997 |
| JP | H09-110631 | 4/1997 |
| JP | H09-202714 | 8/1997 |
| JP | H10-175845 | 6/1998 |
| JP | H11-255619 | 9/1999 |
| JP | 2000-191444 | 7/2000 |
| JP | 2001-31526 | 2/2001 |
| JP | 2001-192559 | 7/2001 |
| WO | WO 98/23251 | 6/1998 |

OTHER PUBLICATIONS

Kirk-Othmer, "Encyclopedia of Chemical Technology," Third Edition, vol. 22, John Wiley & Sons, 1983, pp. 333-433.
English language Derwent Abstract of EP 0 847 752, Jun. 17, 1998.
English language Derwent Abstract of EP 0 923 928, Jun. 23, 1999.
English language Derwent Abstract of EP 1 048 282, Nov. 2, 2000.
English language Derwent Abstract of EP 1 064 920, Jan. 3, 2001.
English language Derwent Abstract of EP 1 082 953, Mar. 14, 2001.

(Continued)

*Primary Examiner*—Jyothsna A. Venkat
(74) *Attorney, Agent, or Firm*—Finnegan, Henderson, Farabow, Garrett & Dunner, LLP

(57) ABSTRACT

A composition for coating keratinous fibers, comprising, in a cosmetically acceptable medium comprising at least one volatile solvent, a nonvolatile fraction comprising: a) at least one polymer capable of adhering to the keratinous fibers, b) particles which are solid at 25° C. chosen from: i) solid particles of a crystalline or semicrystalline material, ii) solid particles of an amorphous material, iii) solid particles of at least one wax having a hardness of greater than or equal to 6.5 MPa iv) and mixtures thereof. The solid particles are present in the composition in an amount such that the volume fraction of the solid particles is less than or equal to 50% of the total volume of the said nonvolatile fraction. The composition can make it possible to obtain good curling of keratinous fibers, such as eyelashes.

97 Claims, No Drawings

OTHER PUBLICATIONS

English language Derwent Abstract of FR 2 792 190, Oct. 20, 2000.
English language Derwent Abstract of FR 2 794 970, Dec. 22, 2000.
David Barthelmy, Maghemite Mineral Data, http://www.webmineral.com/data/Maghemite.shtml.
David Barthelmy, Magnetite Mineral Data, http://www.webmineral.com/data/Magnetite.shtml.
Patent Abstracts of Japan English language abstract of JP H04-210613.
Patent Abstracts of Japan English language abstract of JP H09-202714.
Patent Abstracts of Japan English language abstract of JP H09-2920.
Patent Abstracts of Japan English language abstract of JP H10-175845 and FR 2 756 731.
Patent Abstracts of Japan English language abstract of JP 2001-31526.
French Search Report for FR 01 09502 dated Apr. 22, 2002.
French Search Report for FR 01 09503 dated Apr. 23, 2002.
French Search Report for FR 01 09504 dated May 27, 2002.
French Search Report for FR 01 09505 dated May 27, 2002.
Office Action in co-pending U.S. Appl. No. 10/195,430, dated Nov. 26, 2003.
Office Action in co-pending U.S. Appl. No. 10/195,430, dated May 19, 2004.
Office Action in co-pending U.S. Appl. No. 10/195,430, dated Nov. 22, 2004.
Office Action in co-pending U.S. Appl. No. 10/195,430, dated Aug. 5, 2005.
Office Action in co-pending U.S. Appl. No. 10/195,428, dated Dec. 2, 2003.
Office Action in co-pending U.S. Appl. No. 10/195,428, dated Jun. 25, 2004.
Office Action in co-pending U.S. Appl. No. 10/195,428, dated Apr. 20, 2005.
Office Action in co-pending U.S. Appl. No. 10/195,419, dated Dec. 3, 2003.
Office Action in co-pending U.S. Appl. No. 10/195,419, dated Jun. 3, 2004.
Office Action in co-pending U.S. Appl. No. 10/195,419, dated Mar. 25, 2005.
Notice of Allowance in co-pending U.S. Appl. No. 10/195,419, dated Nov. 14, 2005.
Stedman's Medical Dictionary, 27th Ed. Baltimore: Lippincott, Williams and Wilkins, 2003; http://www.emedicine.com/asp/dictionary.asp?keyword=simethicone, printed on Feb. 28, 2006.

* cited by examiner ary of the invention provides a method for
MASCARA COMPRISING SOLID PARTICLES This application claims priority to U.S. Provisional Application No. 60/306,443, filed Jul. 20, 2001.

One subject of the present invention is a cosmetic composition for coating keratinous fibers, such as eyelashes or hair, comprising solid particles and at least one adherent polymer. The present invention also relates to methods for curling keratinous fibers with the cosmetic compositions described herein. The composition can be applied to substantially longitudinal keratinous fibers of humans, such as eyelashes or hair or alternatively false eyelashes or pastiches such as wigs. The composition can also be used for coating the eyelashes.

The composition may be a make-up composition, also called mascara, a composition to be applied over a make up, also called top coat, or alternatively a composition for treating keratinous fibers, such as eyelashes. In one embodiment, the composition is a mascara.

The present invention can provide a composition for coating eyelashes leading, after application, to a coat, which can confer good curling of the eyelashes.

The inventors have discovered that such a coating of the eyelashes could be obtained using particular solid particles combined with an adherent polymer.

One aspect of the invention provides a composition for coating keratinous fibers, such as eyelashes, comprising, in a cosmetically acceptable medium comprising at least one volatile solvent, a nonvolatile fraction comprising:
a) at least one polymer capable of adhering to the keratinous fibers,
b) main particles which are solid at 25° C. chosen from:
  i) first solid particles comprising at least one first material chosen from crystalline and semicrystalline materials which are solid at 25° C. and have at least one of a first order phase transition, a melting transition and a combustion transition, greater than 100° C.,
  ii) second solid particles comprising a second material chosen from at least one amorphous material having a glass transition temperature of greater than or equal to 60° C.,
  iii) third solid particles comprising a third material chosen from at least one wax having a hardness of greater than or equal to 6.5 MPa, and
  iv) mixtures thereof,
c) and optionally additional solid particles different from the said main solid particles, the additional solid particles not being capable of coalescing at a temperature of less than or equal to 40° C.,
wherein the main solid particles and, where appropriate, the additional solid particles are present in the composition in an amount such that the volume fraction of the main solid particles and, where appropriate, of the additional solid particles is greater than or equal to 1% and less than 50% of the total volume of the said nonvolatile fraction,
and, where appropriate, the volume fraction of the main solid particles is greater than or equal to 50% of the total volume of the main solid particles and of the additional solid particles.

Another aspect of the invention provides a mascara comprising a composition as described herein.

Another aspect of the invention provides a method of applying make-up to or for a nontherapeutic treatment of keratinous fibers, such as eyelashes, comprising applying to the keratinous fibers a composition as described herein.

Another aspect of the invention provides a method for curling keratinous fibers, such as eyelashes, comprising applying to the keratinous fibers in an amount effective to curl the keratinous fibers, a composition as described herein.

Another aspect of the invention provides a method for improving the curling capability of a composition for coating keratinous fibers, the composition comprising, in a cosmetically acceptable medium comprising at least one volatile solvent, a nonvolatile fraction comprising at least one polymer capable of adhering to the keratinous fibers. The method comprises adding main particles to the nonvolatile fraction where the particles are solid at 25° C. and are chosen from:
  i) first solid particles comprising at least one first material chosen from crystalline and semicrystalline materials which are solid at 25° C. and have at least one of a first order phase transition, a melting transition and a combustion transition, greater than 100° C.,
  ii) second solid particles comprising a second material chosen from at least one amorphous material having a glass transition temperature of greater than or equal to 60° C.,
  iii) third solid particles comprising a third material chosen from at least one wax having a hardness of greater than or equal to 6.5 MPa, and
  iv) mixtures thereof,
and optionally additional solid particles different from the main solid particles, the additional solid particles not being capable of coalescing at a temperature of less than or equal to 40° C. the main solid particles and, where appropriate, the additional solid particles being present in the composition in an amount such that the volume fraction of the main solid particles and, where appropriate, of the additional solid particles is greater than or equal to 1% and less than 50% of the total volume of the said nonvolatile fraction,
and, where appropriate, the volume fraction of the main solid particles is greater than or equal to 50% of the total volume of the main solid particles and of the additional solid particles, for curling keratinous fibres, such as eyelashes.

The expression "solid particles" is understood to mean particles which are in the solid state at 25° C. and at atmospheric pressure.

The expression "nonvolatile fraction of the composition" is understood to mean the combination of the constituents present in the composition which are not volatile. The expression "volatile compound" is understood to mean a compound which, taken in isolation, has a non-zero vapor pressure, at room temperature (25° C.) and atmospheric pressure, ranging from $10^{-2}$ to 300 mmHg (1.33 Pa to 40 000 Pa) such as pressures greater than 0.3 mmHg (40 Pa).

In one embodiment, the nonvolatile fraction of the composition can correspond to the mixture of the constituents remaining on the eyelashes after drying of the mascara, containing the composition, applied to the eyelashes.

In one embodiment, to obtain good curling of the eyelashes, the composition according to the invention comprises solid particles, called main solid particles, chosen from the first, second and third solid particles as defined above, and mixtures thereof.

The main solid particles may comprise solid particles, called first solid particles, comprising at least one first material, chosen from crystalline and semicrystalline materials which are solid at 25° C. and have at least one of a first order phase transition, a melting transition and a combustion transition, greater than 100° C., such as greater than 120° C. or greater than 150° C.

The melting or combustion temperature of the first material may be measured according to the ASTM E794-98 standard.

The expression "semicrystalline material" is understood to mean within the context of the invention, a material, such as a polymer, comprising a crystallizable part and an amorphous part exhibiting a reversible first order phase transition temperature, such as a melting point (solid-liquid transition).

The first crystalline or semicrystalline material can exhibit a Vickers hardness greater than or equal to 10, such as a Vickers hardness ranging from 10 to 7500, greater than or equal to 200, ranging from 200 to 7500, greater than or equal to 400, or ranging from 400 to 7500.

The VICKERS hardness (HV) can be determined by applying to the material a penetrometer in the form of a square-base pyramid, using a load P. The mean size of a diagonal of the square impression obtained with the penetrometer can then be measured.

The VICKERS hardness (HV) can then be calculated by the relationship:

$$HV = \frac{1854.4 \times P}{d^2} \quad \begin{array}{l} d = \text{mean diagonal in } \mu m \\ P = \text{load applied in } g \end{array}$$

The measurement of the VICKERS hardness may be carried out using the microdurometer M 400 g 2 from the company LECO.

The first material of the said first solid particles may be an inorganic material which may be chosen from silica, glass, diamond, copper, boron nitride, ceramics, micas, metal oxides for example, iron oxides such as black iron oxide, red iron oxide, yellow iron oxide, titanium oxides, alumina, or alternatively a polymer such as a polyamide, for example nylon, and mixtures thereof.

The said first particles may be solid particles, or alternatively hollow particles.

In one embodiment, the said first particles are formed of the said first material described above.

In one embodiment, the first solid particles comprise at least two different first materials. This is, for example, the case of micas coated with titanium oxide or with iron oxide.

In one embodiment, the said first solid particles comprise at least the said first material, and at least an additional material, different from the said first material, the said first material forming the surface of the said first particles. For these solid particles, the said first material having the characteristics described above exists at the surface of the said first particles, the latter comprising an additional material coated with the first material.

In one embodiment, the said first particles may have a mean size ranging from 5 nm to 50 μm, such as from 20 nm to 50 μm, as measured by methods known to those skilled in the art.

The main solid particles may comprise second solid particles, comprising a second material chosen from at least one amorphous material, such as polymers, having a glass transition temperature greater than or equal to 60° C., such as a glass transition temperature ranging from 60° C. to 800° C., greater than or equal to 80° C., ranging from 80° C. to 700° C., greater than or equal to 100° C., or ranging from 100° C. to 500° C. The glass transition temperature may be measured by DSC (Differential Scanning Calorimetry) according to the ASTM D3418-97 standard.

Representative amorphous materials include polymers which are nonfilm-forming at a temperature of less than or equal to 40° C. having a glass transition temperature as described above.

The expression "nonfilm-forming polymer at a temperature of less than or equal to 40° C." is understood to mean a polymer which is not capable of forming, on its own or in the presence of a film-forming aid, a continuous film which is adherent to a support, such as keratinous fibers, at a temperature of less than or equal to 40° C.

The expression "film-forming aid" is understood to mean plasticizing agents and coalescing agents known to persons skilled in the art for promoting film formation by polymers.

Representative amorphous polymers having a glass transition temperature of greater than or equal to 60° C. include free-radical polymers or polycondensates having the defined glass transition temperature.

As representative free-radical polymers, there may be mentioned:

polymers of ethylene, such as those of cycloethylene and naphthylethylene;
polymers of propylene, such as those of hexafluoropropylene;
acrylic polymers, such those of acrylic acid, dimethyladamanthyl acrylate, and chloroacrylate;
polymers of acrylamide;
polymers methacrylonitrile;
polymers of acetylstyrene, carboxystyrene, and chloromethylstyrene.

As representative polycondensates, there may be mentioned polycarbonates, polyurethanes, polyesters, polyamides, polysulphones, polysulphonamides and carbohydrates such as amylose triacetate.

The second solid particles may be solid particles or hollow particles.

In one embodiment, the second solid particles comprise the second amorphous material described above.

In one embodiment, the second solid particles comprise at least the said second (amorphous) material and at least one additional material, different from the second (amorphous) material, the said second (amorphous) material forming the surface, or the crust, of the said second solid particles and the additional material forming the inside, or the core, of the said second solid particles.

The additional material may be, for example, an additional polymer having a glass transition temperature of less than 60° C., such as less than 45° C.

The second solid particles may be, for example, core-shell particles of polymers comprising an outer part, such as a crust, comprising the second (amorphous) material having a glass transition temperature of greater than or equal to 60° C., and comprising an inner part, such as a core, comprising the additional polymer having a glass transition temperature of less than 60° C.

In one embodiment, the content of the second material in the second solid particles is such that the volume fraction of the second material is greater than or equal to 10%, such as a volume fraction greater than or equal to 30%, by volume of the total volume of the second solid particles.

The second solid particles may have a mean size ranging from 10 nm to 50 μm, such as a mean size ranging from 20 nm to 1 μm, as measured by methods known to those skilled in the art.

As representative second solid particles, there may be used aqueous dispersions of nonfilm-forming polymer which are sold under the names "JONCRYL® SCX 8082", "JONCRYL® 90" by the company JOHNSON POLYMER, "NEOCRYL® XK 52" by the company AVECIA RESINS and "RHODOPAS® 5051" by the company RHODIA CHIMIE.

The main solid particles may comprise third solid particles comprising at least one wax, alternatively called a "hard wax" having a hardness of greater than or equal to 6.5 MPa.

The expression "wax" is understood to mean, within the context of the present invention, a lipophilic fatty compound, which is solid at room temperature (25° C.) and atmospheric pressure (760 mmHg, that is $10^5$ Pa), with a reversible solid/liquid change of state, having a melting point ranging from 30° C. to 99° C., and such as ranging from 45° C. to 99° C.

By heating the wax to its melting point, it is possible to make it miscible with oils and to form a microscopically homogeneous mixture, but on bringing the temperature of the mixture back to room temperature, recrystallization of the wax in the oils of the mixture is obtained.

The melting point values can correspond, according to the invention, to the peak of melting measured using a differential scanning calorimeter (DSC), for example the calorimeter sold under the name DSC 30 by the company METLER, with a rise in temperature of 5 or 10° C. per minute.

The hard wax may have a melting point ranging from 30° C. to 99° C., such as a melting point ranging from 40° C. to 99° C.

The hard wax can have a melting point of greater than or equal to 30° C. and of less than 77° C., such as a melting point greater than or equal to 30° C. and of less than 60° C., such as ranging from 30° C. to 59° C., further such as ranging from 35° C. to 59° C., and or even further such as ranging from 40° C. to 50° C.

The wax may have a hardness ranging from 6.5 MPa to 20 MPa, such as a hardness ranging from 9.7 MPa to 20 MPa, such as ranging from 9.7 MPa to 15 MPa. The wax may have a hardness of greater than 10 MPa, such as a hardness ranging from 10 to 20 MPa, further such as ranging from 10 to 12 MPa.

In one embodiment, the hardness of the wax is determined by measuring the compression force measured at 20° C. using a texturometer sold under the name TA-XT2i by the company RHEO, equipped with a stainless steel cylinder having a diameter of 2 mm, moving at the measuring speed of 0.1 mm/s, and penetrating into the wax at a penetration depth of 0.3 mm. To measure the hardness, the wax is melted at a temperature equal to the melting point of the wax+20° C. The molten wax is poured into a container having a diameter of 30 mm and a depth of 20 mm. The wax is recrystallized at room temperature (25° C.) for 24 hours, and then the wax is stored for at least 1 hour at 20° C. before carrying out the measurement of hardness. The value of the hardness is the measured compacting force divided by the surface area of the texturometer cylinder in contact with the wax.

Representative waxes include Candelilla wax, hydrogenated jojoba wax, sumac wax, ceresin, octacosanyl stearate, tetracontanyl stearate, Shellac wax, behenyl fumarate, di(1, 1,1-trimethylolpropane) tetrastearate sold under the name "HEST 2T-4S" by the company HETERENE, di(1,1,1-trimethylolpropane) tetrabehenate sold under the name HEST 2T-4B by the company HETERENE, and ozokerites such as that sold under the name "OZOKERITE WAX SP 1020 P" by the company STRAHL & PITSCH.

Other exemplary waxes include waxes obtained by hydrogenation of olive oil esterified with stearyl alcohol, sold under the name "PHYTOWAX Olive 18 L 57" and the waxes obtained by hydrogenation of castor oil esterified with cetyl alcohol, sold under the name "PHYTOWAX ricin 16L64 and 22L73" by the company SOPHIM. Such waxes are described in application FR-A-2792190.

The hard wax can be chosen from olive wax obtained by hydrogenation of olive oil esterified with stearyl alcohol, sold under the name PHYTOWAX Olive 18 L 57 by the company SOPHIM and di(1,1,1-trimethylolpropane) tetrastearate.

In one embodiment, the third solid particles may have a mean size ranging from 50 nm to 50 µm, such as a mean size ranging from 50 nm to 10 µm, as measured by methods known to those skilled in the art.

In one embodiment, the main solid particles are chosen from first, second, and third solid particles described above, and mixtures thereof.

In one embodiment, the main solid particles comprise a mixture of the first and second solid particles, or of the second and third solid particles, or of the first and third solid particles described above.

In one embodiment, the main solid particles comprise a mixture of the first, second and third solid particles described above.

The composition according to the invention may comprise, in addition to the first main solid particles described above, additional solid particles, different from the main solid particles.

These additional solid particles can correspond to the particles which are solid at 25° C. of any material, different from the main solid particles, remaining in the form of individualized particles, or optionally of particles stuck together but which retain, in this case, their individual particle state (these particles stuck together are not coalesced at a temperature of less than or equal to 40° C.).

In one embodiment, the constituents present in the composition according to the invention existing in the state of solid particles at 25° C. and which do not coalesce at a temperature of less than or equal to 40° C., on their own or in the presence of the other constituents present in the composition, are considered as being either main solid particles or additional solid particles according to the definitions described above.

The additional solid particles may be made of a material chosen from waxes different from the hard wax of the third particles described above, fillers, polymers different from the amorphous material present in the second solid particles described above.

The additives described below, when they are in the form of solid particles at 25° C., can be either main solid particles, or additional solid particles as described above when these additives possess the corresponding characteristics defined above.

In one embodiment, the at least one adherent polymer present in the composition according to the invention may be in the form of solid particles. In this case, these particles are considered as being solid particles as defined above if this polymer exists as a solid at 25° C. In another embodiment, the adherent polymer particles do not coalesce at a temperature of less than or equal to 40° C.

In the composition according to the invention, the main solid particles and, where appropriate, the additional solid particles are present in an amount such that the volume fraction of the main solid particles and, where appropriate, of the additional solid particles is greater than or equal to 1% and less than 50%, such as a volume fraction greater than or equal to 5% and less than 50%, of the total volume of the nonvolatile fraction of the composition, which means that the total volume of all the first particles and, where appropriate, of the second particles represents at least 1% but less than 50%, such as a volume fraction ranging from 1% to 49% and further such as from 5% to 49%, of the total volume of the nonvolatile fraction of the composition.

The expression "volume fraction of the main solid particles and, where appropriate, of the additional solid particles" is understood to mean the percentage total volume of all the main solid particles and, where appropriate, of all the additional solid particles present in the nonvolatile fraction of the composition, relative to the total volume of all the compounds of the nonvolatile fraction of the composition.

In one embodiment, the said volume fraction of the main solid particles and, where appropriate, of the additional solid particles is greater than or equal to 1% and less than or equal to 40%, such as from 5% to 40%), greater than or equal to 1% and less than or equal to 30%, or from 10% to 30% of the total volume of the nonvolatile fraction of the composition.

The volume fraction (VF) of solid particles present in the nonvolatile fraction of the composition is equal to the percentage total volume V of the said particles divided by the total volume V' of the nonvolatile fraction of the composition.

The volume V of solid particles is equal to the mass m of the said solid particles in the composition divided by the density d of the particles. The density is calculated according to the method described below.

Volume fraction: $VF = 100 \times V/V'$ and $V = m/d$

The total volume V' of the nonvolatile fraction of the composition can be calculated by adding the volume of each nonvolatile constituent present in the composition.

In one embodiment, when the composition comprises additional solid particles as defined above, the main solid particles are present in the composition in an amount such that the volume fraction of the main solid particles is greater than or equal to 50%, such as a volume fraction ranging from 50% to 99%, of the total volume of the main solid particles and of the additional solid particles, further such as greater than or equal to 60%, such as a volume fraction ranging from 60% to 99%, and even further such as greater than or equal to 70%, such as from 70% to 99%.

The volatile solvent present in the composition according to the invention may be chosen from water, the volatile organic solvents and the volatile oils defined below, and mixtures thereof.

In the present application, the expression "polymer capable of adhering to the keratinous fibers", called later adherent polymer, is understood to mean a polymer capable of resting attached to keratinous fibers such as the eyelashes, the hair or the skin, during contact of the polymer with the keratinous fibers. In one embodiment, the adherent polymer is capable of forming a deposit on the keratinous fibers and can remain attached to the latter for a normal period of wear.

In one embodiment, the at least one adherent polymer may be chosen from film-forming polymers at a temperature of less than or equal to 40° C. The expression "film-forming polymer" is understood to mean a polymer capable of forming, on its own or in the presence of a film-forming aid, a continuous deposit such as a film, which adheres to a support, such as keratinous fibers.

The adherent polymer present in the composition according to the invention may be a polymer solubilized or dispersed in the form of solid particles in an aqueous phase of the composition or alternatively solubilized or dispersed in the form of solid particles in at least one liquid fatty phase.

The composition may comprise a mixture of these polymers. When the adherent polymer exists in the form of solid particles, these particles may have a mean particle size ranging from 5 nm to 10 µm, such as a mean particle size ranging from 5 nm to 5 µm, such as from 5 nm to 600 nm, and further such as from 20 nm to 300 nm., as measured by methods known to those skilled in the art.

The adherent polymer may be present in the composition according to the invention in a dry matter content ranging from 0.1% to 50% by weight relative to the total weight of the composition, such as from 0.5% to 40% by weight, and further such as from 1% to 30% by weight.

Representative adherent polymers which can be used in the composition of the present invention, include synthetic polymers of the free-radical type or of the polycondensate type, polymers of natural origin, and mixtures thereof.

The expression "free-radical polymer" is understood to mean a polymer obtained by polymerization of monomers with ethylenic unsaturation, each monomer being capable of homopolymerizing (in contrast to polycondensates).

The polymers of the free-radical type may be vinyl polymers or copolymers or acrylic polymers.

The vinyl polymers may result from the polymerization of ethylenically unsaturated monomers having at least one acid group and/or esters of these acid monomers and/or amides of these acid monomers.

Representative monomers carrying an acid group include α,β-ethylenic unsaturated carboxylic acids such as acrylic acid, methacrylic acid, crotonic acid; maleic acid or itaconic acid.

The esters of acid monomers can be chosen from the esters of acrylic acid and methacrylic acid, also called acrylates or methacrylates, i.e. "(meth)acrylates." In one embodiment, the esters of acid monomers are chosen from alkyl acrylates and alkyl methacrylates, such as $C_1$–$C_{30}$ such as $C_1$–$C_{20}$ alkyl acrylates and $C_1$–$C_{30}$, such as $C_1$–$C_{20}$ alkyl methacrylates. In another embodiment, the esters of acid monomers are chosen from aryl acrylates and aryl methacrylates, such as $C_{6-10}$ aryl acrylates and $C_6$–$C_{10}$ aryl methacrylates. In yet another embodiment, the esters of acid monomers are chosen from hydroxyalkyl acrylates and hydroxyalkyl methacrylates, such as $C_2$–$C_6$ hydroxyalkyl acrylates and $C_2$–$C_6$ hydroxyalkyl methacrylates.

Exemplary alkyl (meth)acrylates include methyl methacrylate, ethyl methacrylate, butyl methacrylate, isobutyl methacrylate, 2-ethylhexyl methacrylate, lauryl methacrylate, and cyclohexyl methacrylate.

Exemplary hydroxyalkyl (meth)acrylates include hydroxyethyl acrylate, 2-hydroxypropyl acrylate, hydroxyethyl methacrylate, and 2-hydroxypropyl methacrylate.

Exemplary aryl (meth)acrylates include benzyl acrylate and phenyl acrylate.

Representative esters of (meth)acrylic acid include alkyl (meth)acrylates.

In one embodiment, the alkyl group of the esters may be either fluorinated or perfluorinated, that is to say that some or all of the hydrogen atoms of the alkyl group are substituted with fluorine atoms.

As amides of the acid monomers, there may be mentioned for example (meth)acrylamides and N-alkyl(meth)acrylamides, such as $C_2$–$C_{12}$ alkyl (meth)acrylamides. Representative N-alkyl(meth)acrylamides include N-ethylacrylamide, N-t-butylacrylamide, N-t-octylacrylamide, and N-undecylacrylamide.

The vinyl polymers may also result from the homopolymerization or copolymerization of monomers chosen from vinyl esters and styrene monomers. In one embodiment, these monomers may be polymerized with acid monomers and/or their esters and/or their amides, such as those mentioned above.

As examples of vinyl esters, there may be mentioned vinyl acetate, vinyl neodecanoate, vinyl pivalate, vinylbenzoate, and vinyl t-butyl benzoate.

As styrene monomers, there may be mentioned styrene and alpha-methylstyrene.

It is possible to use any monomer known to a person skilled in the art entering into the categories of acrylic and vinyl monomers, including the monomers modified by a silicone chain.

Representative polycondensates include polyurethanes, polyesters, polyester amides, polyamides, epoxy ester resins, and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas, polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. There may be mentioned as examples of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecane-dioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid, and 2,6-naphthalenedicarboxylic acid. These dicarboxylic acid monomers may be used alone or in combination with at least two dicarboxylic acid monomers. Representative dicarboxylic acid monomers include phthalic acid, isophthalic acid, and terephthalic acid.

The diol may be chosen from aliphatic, alicyclic, and aromatic diols. Exemplary diols are chosen from: ethylene glycol, diethylene glycol, triethylene glycol, 1,3-propanediol, cyclohexanedimethanol, and 4-butanediol. Representative polyols include glycerol, pentaerythritol, sorbitol, and trimethylolpropane.

The polyester amides may be obtained in a manner similar to the polyesters, by polycondensation of diacids with diamines or amino alcohols. Exemplary diamines include hexamethylenediamine, meta- or para-phenylenediamine. An aminoalcohol, such as monoethanolamine, may be used.

The polyester may, in addition, comprise at least one monomer carrying at least one —$SO_3M$ group, where M is chosen from hydrogen, an ammonium ion such as $NH_4^+$ and an alkali, alkaline-earth or metal ion, such as for example an $Na^+$, $Li^+$, $K^+$, $Mg^{2+}$, $Ca^{2+}$, $Cu^{2+}$, $Fe^{2+}$ and $Fe^{3+}$ ion. A bifunctional aromatic monomer comprising such an —$SO_3M$ group may also be used.

The aromatic ring of the bifunctional aromatic monomer carrying, in addition, an —$SO_3M$ group as described above may be chosen, for example, from benzene, naphthalene, anthracene, diphenyl, oxydiphenyl, sulphonyldiphenyl, and methylenediphenyl rings. There may also be mentioned as examples of a bifunctional aromatic monomer carrying, in addition, an —$SO_3M$ group: sulphoisophthalic acid, sulphoterephthalic acid, sulphophthalic acid, and 4-sulphonaphthalene-2,7-dicarboxylic acid.

Copolymers based on isophthalate/sulphoisophthalate, such as copolymers obtained by condensation of diethylene glycol, cyclohexanedimethanol, isophthalic acid and sulphoisophthalic acid can be used. Such polymers are sold, for example, under the trade name Eastman AQ® by the company Eastman Chemical Products.

The optionally modified polymers of natural origin may be chosen from shellac resin, sandarac gum, dammars, elemis, copals, cellulosic polymers, and mixtures thereof.

In one embodiment, the adherent polymer may be present in the form of solid particles in aqueous dispersion, generally known as latex or pseudolatex. The techniques for preparing these dispersions are well known to persons skilled in the art.

Representative aqueous dispersions of adherent polymer include acrylic dispersions sold under the names NEOCRYL XK-90®, NEOCRYL A-1070®, NEOCRYL A-1090®, NEOCRYL BT-62®, NEOCRYL A-1079®, NEOCRYL A-523® by the company AVECIA-NEORESINS, DOW LATEX 432® by the company DOW CHEMICAL, DAITOSOL 5000 AD® by the company DAITO KASEY KOGYO; or else the aqueous dispersions of polyurethane which are sold under the names NEOREZ R-981®, NEOREZ R-974® by the company AVECIA-NEORESINS, AVALURE UR-405®, AVALURE UR-410®, AVALURE UR-425®, AVALURE UR-450®, SANCURE 875®, SANCURE 861®, SANCURE 878®, SANCURE 2060® by the company GOODRICH, IMPRANIL 85® by the company BAYER, AQUAMERE H-1511® by the company HYDROMER.

Other aqueous dispersions of adherent polymers include dispersions of polymers resulting from the free-radical polymerization of one or more free-radical monomers inside and/or partly at the surface, of preexisting particles of at least one polymer chosen from polyurethanes, polyureas, polyesters, polyesteramides and/or alkyds. These polymers are generally called hybrid polymers.

In one embodiment, the at least one adherent polymer may be a water-soluble polymer and may be present in the aqueous phase of the composition in solubilized form. As examples of film-forming, water-soluble polymers, there may be mentioned proteins such as proteins of plant origin, such as wheat or soya bean proteins; proteins of animal origin such as keratin, for example keratin hydrolysates and sulphonic keratins;

anionic, cationic, amphoteric or nonionic polymers of chitin or chitosan;

cellulose polymers such as hydroxyethyl cellulose, hydroxypropyl cellulose, methyl cellulose, ethyl hydroxyethyl cellulose, carboxymethyl cellulose, and quaternized derivatives of cellulose;

acrylic polymers or copolymers such as polyacrylates or polymethacrylates;

vinyl polymers, such as polyvinylpyrrolidones, copolymers of methyl vinyl ether and maleic anhydride, the copolymer of vinyl acetate and crotonic acid, copolymers of vinylpyrrolidone and vinyl acetate;

copolymers of vinylpyrrolidone and caprolactam; polyvinyl alcohol;

optionally modified polymers of natural origin, such as:
  gum arabic, guar gum, xanthan derivatives, karaya gum;
  alginates and carrageenans;
  glycoaminoglycans, hyaluronic acid and its derivatives;
  shellac resin, sandarac gum, dammars, elemis, copals;
  deoxyribonucleic acid;

muccopolysaccharides such as hyaluronic acid, chondroitin sulphates, and mixtures thereof.

In one embodiment, the at least one adherent polymer may be present in at least one liquid fatty phase chosen from oils and organic solvents such as those described above. The expression "liquid fatty phase" is understood to mean, in the context of the invention, a fatty phase which is liquid at room temperature (25° C.) and atmospheric pressure (760 mmHg, that is $10^5$ Pa), comprising one or more fatty substances which are liquid at room temperature, also called oils, which are generally compatible with each other.

In one embodiment, the liquid fatty phase comprises a volatile oil, optionally in the form of a mixture with a nonvolatile oil, it being possible for the oils to be chosen from the oils cited below.

In one embodiment of the composition, the at least one adherent polymer may be present in the form of surface-stabilized particles dispersed in the liquid fatty phase.

The dispersion of surface-stabilized polymer particles may be manufactured as described in the document EP-A-749747.

The polymer particles can be surface-stabilized using a stabilizer which may be a block polymer, a graft polymer and/or a random polymer, alone or in the form of a mixture.

Exemplary dispersions of film-forming polymer in the liquid fatty phase, in the presence of stabilizing agents, are described in the documents EP-A-749746, EP-A-923928, and EP-A-930060, the disclosures of which are incorporated by reference herein.

The size of the polymer particles in dispersion either in the aqueous phase or in the liquid fatty phase may range from 5 nm to 600 nm, such as from 20 nm to 300 nm, as measured by methods known to those skilled in the art.

In one embodiment, the adherent polymer may be solubilized in the liquid fatty phase. In one embodiment, the film-forming polymer can be a fat-soluble polymer.

By way of example of a fat-soluble polymer, there may be mentioned copolymers of vinyl ester (the vinyl group being directly linked to the oxygen atom of the ester group and the vinyl ester having a linear or branched saturated hydrocarbon radical of 1 to 19 carbon atoms, linked to the carbonyl of the ester group) and of at least one other monomer which may be a vinyl ester different from the vinyl ester already present, an α-olefin such as α-olefins having from 8 to 28 carbon atoms, an alkyl vinyl ether such as alkyl vinyl ethers where the alkyl group comprises from 2 to 18 carbon atoms, or an allyl or methallyl ester such as those esters having a linear or branched saturated hydrocarbon radical of 1 to 19 carbon atoms, linked to the carbonyl of the ester group.

These copolymers may be crosslinked using crosslinking agents which may be either of the vinyl type, or of the allyl or methallyl type, such as tetraallyloxyethane, divinylbenzene, divinyl octanedioate, divinyl dodecanedioate, and divinyl octadecanedioate.

As examples of these copolymers, there may be mentioned the copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl propionate/vinyl stearate, allyl dimethyl propionate/vinyl stearate, vinyl propionate/vinyl stearate, crosslinked with 0.2% of divinylbenzene, vinyl dimethyl propionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene crosslinked with 0.2% of divinylbenzene, and allyl propionate/allyl stearate crosslinked with 0.2% of divinylbenzene.

Representative fat-soluble polymers include fat-soluble homopolymers, such as those resulting from the homopolymerization of vinyl esters having from 9 to 22 carbon atoms or of alkyl acrylates or methacrylates, the alkyl radicals having from 10 to 20 carbon atoms.

Such fat-soluble homopolymers may be chosen from polyvinyl stearate, polyvinyl stearate crosslinked using divinylbenzene, diallyl ether and diallyl phthalate, polystearyl (meth)acrylate, polyvinyl laurate, and polylauryl (meth)acrylate, it being possible for these poly(meth)acrylates to be crosslinked using ethylene glycol or tetraethylene glycol dimethacrylate.

The fat-soluble copolymers and homopolymers defined above are known and exemplary copolymers and homopolymers are described in application FR-A-2232303; they may have a weight-average molecular weight ranging from 2,000 to 500,000, such as from 4,000 to 200,000.

Representative film-forming fat-soluble polymers which can be used in the invention include polyalkylenes, for example copolymers of $C_2$–$C_{20}$ alkenes, such as polybutene, alkyl celluloses with a saturated or unsaturated, linear or branched, $C_1$ to $C_8$ alkyl radical such as ethyl cellulose and propyl cellulose, copolymers of vinylpyrrolidone (VP) such as copolymers of vinylpyrrolidone and of a $C_2$ to $C_{40}$, such as $C_3$ to $C_{20}$, alkene. By way of example of a VP copolymer which can be used in the invention, there may be mentioned the VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene and VP/acrylic acid/lauryl methacrylate copolymer.

The composition according to the invention may comprise a film-forming aid which promotes the formation of a film with the film-forming polymer. Such a film-forming agent may be chosen from all the compounds known to persons skilled in the art to be capable of fulfilling the desired function, and may be chosen from plasticizing agents and coalescing agents.

In one embodiment, the at least one adherent polymer may be chosen from polymers capable of forming a deposit, such as a film, producing, at a concentration of 7% in water, a retraction of isolated stratum corneum of more than 1% at 30° C. under a relative humidity of 40%, such as a retraction of more than 1.2%, or more than 1.5%. This retraction can be measured using an extensiometer, according to the method described below.

In one embodiment, the composition may comprise an aqueous medium comprising an aqueous phase, which may be the continuous phase of the composition.

The aqueous phase may consist essentially of water or it may also comprise a mixture of water and a water-miscible solvent. A water-miscible solvent is a solvent capable of forming with water a homogeneous mixture transparent to the eye at 25° C. Exemplary water-miscible solvents include lower monoalcohols having from 1 to 5 carbon atoms such as ethanol, isopropanol; glycols having from 2 to 8 carbon atoms such as propylene glycol, ethylene glycol, 1,3-butylene glycol, dipropylene glycol; $C_3$–$C_4$ ketones; and $C_2$–$C_4$ aldehydes.

The aqueous phase (water and optionally the water-miscible organic solvent), may be present in an amount ranging from 1% to 95% by weight, relative to the total weight of the composition, such as from 3% to 80% by weight, and further such as from 5% to 60% by weight.

In one embodiment, the composition may comprise at least one volatile organic solvent or oil. The at least one volatile organic solvent or oil may form a fatty phase, such as a continuous fatty phase. The composition may be an anhydrous composition.

The expression "volatile organic solvent or oil" is understood to mean, in the context of the invention, volatile cosmetic oils and organic solvents, which are liquid at room temperature, having a non-zero vapor pressure, at room temperature and atmospheric pressure, ranging, for example, from $10^{-2}$ to 300 mmHg (1.33 Pa to 40 000 Pa) such as a pressure greater than 0.3 mmHg (30 Pa). The expression "nonvolatile oil" is understood to mean an oil having a vapor pressure of less than $10^{-2}$ mmHg (1.33 Pa) at room temperature and atmospheric pressure.

These oils may be hydrocarbon oils, silicone oils, fluorinated oils, or mixtures thereof.

The expression "hydrocarbon oil" is understood to mean an oil containing mainly hydrogen and carbon atoms and optionally oxygen, nitrogen, sulphur and phosphorus atoms. The volatile hydrocarbon oils may be chosen from hydrocarbon oils having from 8 to 16 carbon atoms, for example $C_8$–$C_{16}$ alkanes such as $C_8$–$C_{16}$ isoalkanes of petroleum origin (also called isoparaffins) such as isododecane (also called 2,2,4,4,6-pentamethylheptane), isodecane, isohexadecane, and for example the oils sold under the trade names Isopars' or Permetyls, $C_8$–$C_{16}$ branched esters, isohexyl neopentanoate, and mixtures thereof. Other volatile hydrocarbon oils such as petroleum distillates, such as those oils sold under the name Shell Solt by the company SHELL, may also be used. The volatile solvent can be chosen from volatile hydrocarbon oils having from 8 to 16 carbon atoms and mixtures thereof.

Representative volatile oils include volatile silicones, for example volatile linear or cyclic silicone oils, such as those having a viscosity $\leq 8$ centistokes ($8 \times 10^{-6}$ m$^2$/s), and having, for example, from 2 to 7 silicon atoms, these silicones optionally comprising alkyl or alkoxy groups having from 1 to 10 carbon atoms. As volatile silicone oil which can be used in the invention, there may be mentioned octamethylcyclotetrasiloxane, decamethylcyclopentasiloxane, dodecamethylcyclohexa-siloxane, heptamethylhexyltrisiloxane, heptamethyl-octyltrisiloxane, hexamethyldisiloxane, octamethyltri-siloxane, decamethyltetrasiloxane, dodecamethylpenta-siloxane, and mixtures thereof.

The volatile oil may be present in the composition according to the invention in an amount ranging from 0.1% to 98% by weight, relative to the total weight of the composition, such as an amount ranging from 1% to 65% by weight.

The composition may also comprise at least one nonvolatile oil chosen from nonvolatile hydrocarbon and/or silicone and/or fluorinated oils.

Exemplary nonvolatile hydrocarbon oils include:

hydrocarbon oils of plant origin such as triglycerides comprising, esters of fatty acids and of glycerol in which the fatty acids may have varying chain lengths from $C_4$ to $C_{24}$, it being possible for the latter to be linear or branched, saturated or unsaturated; exemplary hydrocarbon oils include wheatgerm oil, sunflower oil, grapeseed oil, sesame oil, maize oil, apricot oil, castor oil, karite oil, avocado oil, olive oil, soyabean oil, sweet almond oil, palm oil, rapeseed oil, cottonseed oil, hazelnut oil, macadamia oil, jojoba oil, lucerne oil, poppyseed oil, pumpkinseed oil, sesame oil, gourd oil, rapeseed oil, blackcurrant seed oil, evening primrose oil, millet oil, barley oil, quinoa oil, rye oil, safflower oil, candlenut oil, passionflower oil, rose-muscat oil; as well as triglycerides of caprylic/capric acids such as those sold by the company Stearineries Dubois or those sold under the names Miglyol 810, 812 and 818 by the company Dynamit Nobel, synthetic ethers having from 10 to 40 carbon atoms;

linear or branched hydrocarbons of mineral or synthetic origin such as petroleum jelly, polydecenes, hydrogenated polyisobutene such as parleam, squalane, and mixtures thereof;

synthetic esters such as the oils of formula $R_1COOR_2$ in which $R_1$ is a residue of a linear or branched fatty acid comprising from 1 to 40 carbon atoms and $R_2$ is a hydrocarbon chain, such as a branched hydrocarbon chain, containing from 1 to 40 carbon atoms provided that $R_1+R_2$ is $\geq 10$, such as for example Purcellin oil (ketostearyl octanoate), isopropyl myristate, isopropyl palmitate, $C_{12}$ to $C_{15}$ alcohol benzoate, hexyl laurate, diisopropyl adipate, isononyl isononanoate, 2-ethylhexyl palmitate, isostearyl isostearate, octanoates, decanoates or ricinoleates of alcohols or of polyalcohols such as propylene glycol dioctanoate; hydroxylated esters such as isostearyl lactate, diisostearyl malate; and esters of pentaerythritol;

fatty alcohols which are liquid at room temperature containing a branched and/or unsaturated carbon chain comprising from 12 to 26 carbon atoms such as octyl dodecanol, isostearyl alcohol, oleyl alcohol, 2-hexyldecanol, 2-butyloctanol, 2-undecylpentadecanol;

higher fatty acids such as oleic acid, linoleic acid, and linolenic acid; and mixtures thereof.

The nonvolatile silicone oils which can be used in the composition according to the-invention may be nonvolatile polydimethylsiloxanes (PDMS), polydimethylsiloxanes comprising alkyl or alkoxy groups, pendant and/or at the silicone chain end, the alkyl and alkoxy groups each having from 2 to 24 carbon atoms, phenylated silicones such as phenyltrimethicones, phenyldimethicones, phenyltrimethylsiloxydi-phenylsiloxanes, diphenyldimethicones, diphenylmethyl-diphenyltrisiloxanes, and (2-phenylethyl)trimethylsioloxy-silicates.

The fluorinated oils which can be used in the invention include fluorosilicone oils, fluorinated polyethers, fluorinated silicones, such as those as described in the document EP-A-847752.

The nonvolatile oils may be present in the composition according to the invention in an amount ranging from 0.1% to 50% by weight, such as from 0.1% to 30% by weight, relative to the total weight of the composition, and further such as from 0.1% to 20% by weight relative to the total weight of the composition.

The composition according to the invention may comprise, in addition, at least one additional wax different from the wax of the third solid particles described above.

Exemplary additional waxes include beeswax, lanolin wax, Chinese wax, rice wax, Carnauba wax, certain microcrystalline waxes, paraffin waxes, certain ozokerites, certain polyethylene waxes, and certain waxes obtained by Fisher-Tropsch synthesis.

Other representative waxes include those obtained by catalytic hydrogenation of animal or vegetable oils having linear or branched $C_8$–$C_{32}$ fatty chains. Among these, exemplary waxes include hydrogenated sunflower oil, hydrogenated castor oil, hydrogenated copra oil and hydrogenated lanolin oil. Silicon waxes or fluorinated waxes may also be used.

The additional wax present in the composition may be dispersed in the form of particles in the aqueous medium of the composition. These particles may have a mean size ranging from 50 nm to 50 µm, and such as from 50 nm to 10 µm, as measured by methods known to those skilled in the art.

In one embodiment, the additional wax can be present in the composition according to the invention in the form of solid particles and form part of the additional solid particles defined above.

The additional wax may be present in the composition according to the invention in an amount ranging from 0.1% to 50% by weight, relative to the total weight of the composition, such as from 0.5% to 30% by weight, or from 1% to 20% by weight.

The composition according to the invention may contain at least one surfactant, such as emulsifying surfactants. The at least one surfactant may be present in an amount ranging from 2 to 30% by weight relative to the total weight of the composition, such as from 5% to 15%. The at least one surfactant may be chosen from anionic and nonanionic surfactants. Reference may be made to the document "Encyclopedia of Chemical Technology, KIRK-OTHMER", volume 22, p. 333–432, $3^{rd}$ edition, 1979, WILEY, for the definition of the properties and functions (emulsifier) of the surfactants, for example, p. 347–377 of this reference, for anionic and nonionic surfactants.

Exemplary surfactants used in the composition according to the invention may be chosen from:
  nonionic surfactants: fatty acids, fatty alcohols, polyethoxylated or polyglycerolated fatty alcohols such as polyethoxylated stearyl or cetylstearyl alcohols, esters of fatty acid and of sucrose, esters of alkyl glucose, such as polyoxyethylenated fatty esters of $C_1$–$C_6$ alkyl glucose, and mixtures thereof;
  anionic surfactants: $C_{16}$–$C_{30}$ fatty acids neutralized with amines, aqueous ammonia or alkaline salts and mixtures thereof; oxyethylenated acrylic acid/monostearyl itaconate copolymer (20 EO) as an aqueous dispersion at 30% by weight sold under the name "STRUCTURE 2001" by the company National Starch, ethoxylated acrylic acid/monocetyl itaconate copolymer (20 EO) as an aqueous dispersion at 30% sold under the name "STRUCTURE 3001" by the company National Starch.

In one embodiment, the at least one surfactant allow the production of an oil-in-water or wax-in-water emulsion.

The composition according to the invention may also comprise a coloring substance such as pulverulent coloring substances, fat-soluble colorants, water-soluble colorants. This coloring substance may be present in an amount ranging from 0.01% to 50% by weight, relative to the total weight of the composition, such as from 0.01% to 30% by weight.

The pulverulent coloring substances may be chosen from pigments and pearlescent agents.

The pigments may be white or colored, inorganic and/or organic, coated or otherwise. Representative inorganic pigments include titanium dioxide, optionally surface-treated, zirconium, zinc or cerium oxides, as well as iron or chromium oxides, manganese violet, ultramarine blue, chromium hydrate and ferric blue. Representative organic pigments include carbon black, pigments of the D & C type, and lacquers based on carmine, barium, strontium, calcium or aluminium.

The pearlescent agents may be chosen from white pearlescent pigments such as mica coated with titanium or bismuth oxychloride, colored pearlescent pigments such as mica-titanium with iron oxides, mica-titanium with ferric blue or chromium oxide, mica-titanium with an organic pigment of the abovementioned type as well as pearlescent pigments based on bismuth oxychloride.

The fat-soluble colorants include, for example, Sudan red, D&C Red 17, D&C Green 6, β-carotene, soyabean oil, Sudan brown, D&C Yellow 11, D&C Violet 2, D&C Orange 5, quinoline yellow, annatto. The water-soluble colorants include, for example, sugarbeet juice and methylene blue.

The composition of the invention may comprise, in addition, any additive conventionally used in cosmetics, such as antioxidants, fillers, preservatives, perfumes, neutralizing agents, thickeners, plasticizers, coalescing agents, cosmetic or dermatological active agents such as, for example, emollients, moisturizers, vitamins, sunscreens, and mixtures thereof. These additives may be present in the composition in an amount ranging from 0.01 to 20% of the total weight of the composition, such as from 0.01 to 10% (if present).

The composition according to the invention may be provided in the form of an oil-in-water emulsion, a water-in-oil emulsion, a wax-in-water dispersion or alternatively may be an anhydrous composition.

Of course persons skilled in the art will be careful to choose the possible additional additives and/or their quantity such that the advantageous properties of the composition according to the invention are not or not substantially impaired by the addition envisaged.

The composition according to the invention may be manufactured by known methods which are generally used in the cosmetic or dermatological field.

In one embodiment, the composition according to the invention does not contain:
  a) a mixture of 41% of water, 10% of isododecane, 5% of ethanol, 4% of hectorite, and 10% of black iron oxide; or
  b) a mixture of 62.9% of water, 10% of stearic acid, 3% of triethanolamine, 4% of zinc oxide, and 10% of black iron oxide, the percentages being expressed by weight relative to the total weight of the composition.

The invention is illustrated in greater detail in the following examples.

Method of Measuring the Density of Solid Particles:

The apparent density of solid particles is measured using a Gay-Lussac pycnometer.

A precision scale (precision of 1 mg) is used and the measurements are carried out in a thermostatic chamber at 25° C. (±0.5° C.). Two reference liquids having a density d, which are demineralized water (d=1000 kg/m$^3$) and heptane (d=683.7 kg/m$^3$) are also used. The density of the solid particles is measured with each reference liquid.

The pycnometer and the products used for carrying out the measurement are placed at the temperature of 25° C. The masses cited below are expressed in kilograms.

The mass M0 of the pycnometer is measured, then the pycnometer is completely filled with the reference liquid used, avoiding introducing air bubbles. The mass M1 of the filled pycnometer is measured.

A mixture of mass M2 of the material whose density d2 it is desired to measure with a mass M3 of reference liquid is then prepared. The mixture is stirred and then just before the end of stirring, the pycnometer is filled with this mixture and the mass M4 of the filled pycnometer is measured. The mass M4−M0 of the mixture present in the pycnometer is thus measured.

The pycnometer having a constant filling volume, it is therefore possible to establish the following relationship:
(M1−M0)/d=(M2/d2+M3/d)×(M4−M0)/(M2+M3)    This relationship makes it possible to calculate the value of the density d2 of the solid particles, expressed in kg/m³. A value of the density of the solid particles is thus determined for each of the reference liquids. The highest value (among the density measured with distilled water and the density measured with heptane) is selected as value of the density for the determination of the volume fraction of the solid particles.

Method for Measuring Retraction:

The length of a test piece of isolated stratum corneum is measured before treatment and after treatment, followed by determining the percentage retraction of the test piece.

Test pieces of 1 cm×0.4 cm of stratum corneum are used which have a thickness ranging from 10 to 20 µm placed on the extensiometer MTT 610 marketed by the company DIASTRON.

The test piece is placed between 2 jaws and left for 12 hours in an atmosphere at 30° C. and 40% relative humidity.

The test piece is drawn, at the rate of 2 mm/minute, by a length of between 5 and 10% of the initial length in order to determine the length $l_1$ from which the test piece begins to exert a force on the jaws and which is detected by the apparatus.

The test piece is then relaxed and then 2 mg of an aqueous composition containing 7% by weight of polymer are applied to the stratum corneum. After evaporation of water from the composition, the test piece is drawn under the same conditions as those described above in order to also determine the length $l_2$ for the treated test piece.

The percentage retraction is determined by the ratio: $100 \times (l_2 - l_1)/l_1$.

EXAMPLE 1 a) An aqueous beeswax dispersion is prepared by mixing, at 95° C., 40 g of beeswax, 4 g of polyoxyethylenated lauryl alcohol surfactant containing 23 ethylene oxide units sold under the name "BRIJ 35" by the company UNICHEMA and 56 g of water heated to 95° C., with stirring using an Ultraturrax stirrer, until an aqueous wax dispersion having a mean particle size of about 300 nm is obtained.

b) A mascara having the following composition is prepared:

| | |
|---|---|
| Polyurethane as a 35% aqueous dispersion of polymer (AVALURE UR 410 from Goodrich) | 30 g AS |
| Beeswax | 3 g |
| Nylon-12 powder (Orgasol 2002 from Atochem) | 5 g |
| Black iron oxide (Sicovit black 85E172 from BASF) | 5 g |
| Hydroxyethylcellulose (Cellosize QP4400M from Amerchol) | 1 g |
| Propylene glycol | 5 g |
| Surfactant (Brij 35) | 0.3 g |
| Water | qs 100 g |

This composition is prepared by mixing 7.5 g of the wax dispersion described in point a) above with the complementary aqueous fraction comprising the other ingredients.

A mascara is obtained whose nonvolatile fraction (formed of all the constituents except water) contains a volume fraction of solid particles (wax, nylon, black iron oxide) equal to 28% (relative to the total volume of the nonvolatile fraction); the volume fraction of the main particles in the context of the present invention (black iron oxide and nylon) represents 78.6% of the total volume of the solid particles.

The eyelashes to which this mascara has been applied as make-up exhibit good curling.

EXAMPLE 2

A mascara having the following composition is prepared:

| | |
|---|---|
| Polyurethane as a 35% aqueous dispersion of polymer (AVALURE UR 410 from Goodrich) | 15 g AS |
| Styrene acrylic copolymer as a 30% aqueous dispersion of polymer (Joncryl SCX 8082 from Johnson Polymers)* | 6.5 g AS |
| Black iron oxide (Sicovit black 85E172 from BASF) | 2.5 g |
| Hydroxyethylcellulose (Cellosize QP4400M from Amerchol) | 0.5 g |
| Propylene glycol | 2.5 g |
| Water | qs 100 g |

*latex having a glass transition temperature Tg = 102° C.

A mascara is obtained whose nonvolatile fraction (formed of all the constituents except water) contains a volume fraction of solid particles (styrene/acrylic copolymer, black iron oxide) equal to 28% (relative to the total volume of the nonvolatile fraction); the volume fraction of the main particles in the context of the present invention (black iron oxide and styrene/acrylic copolymer) represents 100% of the total volume of the solid particles.

The eyelashes to which this mascara has been applied as make-up exhibit good curling.

EXAMPLE 3 a) A dispersion of hard wax is prepared by mixing, at 95° C., 40 g of wax sold under the name "PHYTOWAX Olive 18 L 57" by the company SOPHIM, 4 g of polyoxyethylenated lauryl alcohol surfactant containing 23 ethylene oxide units sold under the name "BRIJ 35" by the company UNICHEMA and 56 g of water heated to 95° C., with stirring using an Ultraturrax stirrer, until an aqueous wax dispersion having a mean particle size of about 300 nm is obtained.

b) A mascara having the following composition is prepared:

| | |
|---|---|
| Polyurethane as a 35% aqueous dispersion of polymer (AVALURE UR 410 from Goodrich) | 30 g AS |
| Wax (PHYTOWAX Olive 18 L 57 from the company SOPHIM) | 13 g |
| Black iron oxide (Sicovit black 85E172 from BASF) | 5 g |
| Hydroxyethylcellulose (Cellosize QP4400M from Amerchol) | 1 g |
| Propylene glycol | 5 g |
| Surfactant (Brij 35) | 1.3 g |
| Water | qs 100 g |

This composition is prepared by mixing 32.5 g of the wax dispersion described in point a) above with the complementary aqueous fraction comprising the other ingredients.

A mascara is obtained whose nonvolatile fraction (formed of all the constituents except water) contains a volume fraction of solid particles (wax, black iron oxide) equal to 28% (relative to the total volume of the nonvolatile fraction); the volume fraction of the main particles in the context of the present invention (black iron oxide and wax) represents 100% of the total volume of the solid particles.

The eyelashes to which this mascara has been applied as make-up exhibit good curling.

What is claimed is:

1. A composition for coating keratinous fibers, comprising, in a cosmetically acceptable medium comprising at least one volatile solvent, a nonvolatile fraction comprising:
   a) at least one polymer capable of adhering to the keratinous fibers,
   b) main particles which are solid at 25° C. chosen from:
      i) first solid particles comprising at least one first material chosen from crystalline and semicrystalline materials which are solid at 25° C. and have at least one of a first order phase transition, a melting transition and a combustion transition, greater than 100° C.,
      ii) second solid particles comprising a second material chosen from at least one amorphous material having a glass transition temperature of greater than or equal to 60° C.,
      iii) third solid particles comprising a third material chosen from at least one wax having a hardness of greater than or equal to 6.5 MPa, and
      iv) mixtures thereof,
   c) and optionally additional solid particles different from said main solid particles, the additional solid particles not being capable of coalescing at a temperature of less than or equal to 40° C.,
   wherein the main solid particles and, where appropriate, the additional solid particles are present in the composition in an amount such that the volume fraction of the main solid particles and, where appropriate, of the additional solid particles is greater than or equal to 1% and less than 50% of the total volume of said nonvolatile fraction,
   and, where appropriate, the volume fraction of the main solid particles is greater than or equal to 50% of the total volume of the main solid particles and of the additional solid particles.

2. The composition according to claim 1, wherein the keratinous fibers are eyelashes.

3. The composition according to claim 1, wherein the main particles comprise the first solid particles, and the at least one first material has a first order phase transition greater than 100° C.

4. The composition according to claim 3, wherein the at least one first material has a first order phase transition greater than 120° C.

5. The composition according to claim 4, wherein the at least one first material has a first order phase transition greater than 150° C.

6. The composition according to claim 1, wherein the at least one first material has a Vicker hardness of greater than or equal to 10.

7. The composition according to claim 6, wherein the at least one first material has a Vicker hardness ranging from 10 to 7,500.

8. The composition according to claim 1, wherein the at least one first material has a Vicker hardness greater than or equal to 200.

9. The composition according to claim 8, wherein the at least one first material has a Vicker hardness ranging from 200 to 7,500.

10. The composition according to claim 9, wherein the at least one first material has a Vicker hardness greater than or equal to 400.

11. The composition according to claim 10, wherein the at least one first material has a Vicker hardness ranging from 400 to 7,500.

12. The composition according to claim 1, wherein the at least one first material is chosen from silica, glass, diamond, copper, boron nitride, ceramics, metal oxides, and polyamides.

13. The composition according to claim 12, wherein the metal oxides are chosen from iron oxides.

14. The composition according to claim 1, wherein the first solid particles have a mean size ranging from 5 nm to 50 nm.

15. The composition according to claim 14, wherein the first solid particles have a mean size ranging from 20 nm to 50 nm.

16. The composition according to claim 1, wherein the main particles comprise the second solid particles, and the second material has a glass transition temperature greater than or equal to 60° C.

17. The composition according to claim 16, wherein the second material has a glass transition temperature greater than or equal to 80° C.

18. The composition according to claim 17, wherein the second material has a glass transition temperature greater than or equal to 100° C.

19. The composition according to claim 1, wherein the second material is at least one polymer.

20. The composition according to claim 19, wherein the second material is at least one polymer chosen from free-radical polymers and polycondensates.

21. The composition according to claim 20, wherein the second material is at least one polymer chosen from ethylene polymers, propylene polymers, acrylic polymers, acrylamide polymers, acrylonitrile polymers, methacrylonitrile polymers, polycarbonates, polyurethanes, polyesters, polyamides, polysulphones, polysulphonamides, and carbohydrates.

22. The composition according to claim 1, wherein the second particles have a mean size ranging from 10 nm to 50 μm.

23. The composition according to claim 22, wherein the second particles have a mean size ranging from 20 nm to 1 μm.

24. The composition according to claim 1, wherein the main particles comprise the third solid particles.

25. The composition according to claim 1, wherein the third material comprises at least one wax having a melting point ranging from 30° C. to 99° C.

26. The composition according to claim 25, wherein the at least one wax has a melting point ranging from 40° C. to 99° C.

27. The composition according to claim 26, wherein the at least one wax has a melting point greater than or equal to 30° C. and less than 77° C.

28. The composition according to claim 27, wherein the at least one wax has a melting point greater than or equal to 30° C. and less than 60° C.

29. The composition according to claim 25, wherein the at least one wax has a hardness ranging from 6.5 MPa to 20 MPa.

30. The composition according to claim 29, wherein the at least one wax has a hardness ranging from 6.5 MPa to 15 MPa.

31. The composition according to claim 30, wherein the at least one wax has a hardness ranging from 6.5 to 12 MPa.

32. The composition according to claim 29, wherein the at least one wax has a hardness ranging from 9.7 to 20 MPa.

33. The composition according to claim 32, wherein the at least one wax has a hardness ranging from 9.7 to 15 MPa.

34. The composition according to claim 33, wherein the at least one wax has a hardness ranging from 9.7 to 12 to MPa.

35. The composition according to claim 1, wherein the at least one wax is chosen from Candelilla wax, hydrogenated jojoba wax, sumac wax, ceresin, octacosanyl stearate, tetracontanyl stearate, Shellac wax, behenyl fumarate, di(1,1,1-trimethylolpropane) tetrastearate, di(1,1,1-trimethylolpropane) tetrabehenate, ozokerites, waxes obtained by hydrogenation of olive oil esterified with stearyl alcohol, and waxes obtained by hydrogenation of castor oil esterified with cetyl alcohol.

36. The composition according to claim 1, wherein the at least one wax is chosen from di(1,1,1-trimethylolpropane) tetrastearate and olive waxes obtained by hydrogenation of olive oil esterified with stearyl alcohol.

37. The composition according to claim 1, wherein the third solid particles have a mean size ranging from 50 nm to 50 µm.

38. The composition according to claim 37, wherein the third solid particles have a mean size ranging from 100 nm to 10 µm.

39. The composition according to claim 1, wherein the composition comprises said main particles and said additional solid particles.

40. The composition according to claim 1, wherein the volume fraction of the main particles and, where appropriate, of the additional solid particles ranges from 1% to 49% of the total volume of the nonvolatile fraction of the composition.

41. The composition according to claim 40, wherein the volume fraction of the main particles and, where appropriate, of the additional solid particles is greater than or equal to 5% and less than 50% of the total volume of the nonvolatile fraction of the composition.

42. The composition according to claim 41, wherein the volume fraction of the main particles and, where appropriate, of the additional solid particles ranges from 5% to 49% of the total volume of the nonvolatile fraction of the composition.

43. The composition according to claim 40, wherein the volume fraction of the main particles and, where appropriate, of the additional solid particles is greater than or equal to 1% and less than or equal to 40% of the total volume of the nonvolatile fraction of the composition.

44. The composition according to claim 43, wherein the volume fraction of the main particles and, where appropriate, of the additional solid particles ranges from 5% to 40% of the total volume of the nonvolatile fraction of the composition.

45. The composition according to claim 40, wherein the volume fraction of the main particles and, where appropriate, of the additional solid particles is greater than or equal to 1% and less than or equal to 30% of the total volume of the nonvolatile fraction of the composition.

46. The composition according to claim 45, wherein the volume fraction of the main particles and, where appropriate, of the additional solid particles ranges from 10% to 30% of the total volume of the nonvolatile fraction of the composition.

47. The composition according to claim 39, wherein the main particles are present in the composition in an amount such that the volume fraction of the main particles is greater than or equal to 50% of the total volume of the main particles and of the additional solid particles.

48. The composition according to claim 47, wherein the main particles are present in the composition in an amount such that the volume fraction of the main solid particles ranges from 50% to 99%, of the total volume of the main particles and of the additional solid particles.

49. The composition according to claim 47, wherein the main particles are present in the composition in an amount such that the volume fraction of the main particles is greater than or equal to 60%, of the total volume of the main particles and of the additional solid particles.

50. The composition according to claim 49, wherein the main particles are present in the composition in an amount such that the volume fraction of the main particles ranges from 60% to 99%, of the total volume of the main particles and of the additional solid particles.

51. The composition according to claim 47, wherein the main particles are present in the composition in an amount such that the volume fraction of the main particles is greater than or equal to 70%, of the total volume of the main particles and of the additional solid particles.

52. The composition according to claim 51, wherein the main particles are present in the composition in an amount such that the volume fraction of the main particles ranges from 70% to 99%, of the total volume of the main particles and of the additional solid particles.

53. The composition according to claim 1, wherein the at least one volatile solvent is chosen from water, volatile organic solvents, and volatile oils.

54. The composition according to claim 1, wherein the at least one polymer capable of adhering to the keratinous fibers is chosen from vinyl polymers, polyurethanes, polyesters, polyamides, polyureas, and cellulose polymers.

55. The composition according to claim 1, wherein the at least one polymer capable of adhering to the keratinous fibers is a film-forming polymer at a temperature of less than or equal to 40° C.

56. The composition according to claim 1, wherein the at least one polymer capable of adhering to the keratinous fibers is capable of forming a deposit producing, at a concentration of 7% in water, a retraction of the isolated stratum corneum of more than 1% at 30° C. at a relative humidity of 40%.

57. The composition according to claim 56, wherein the retraction of the stratum corneum is more than 1.2%.

58. The composition according to claim 57, wherein the retraction of the stratum corneum is more than 1.5%.

59. The composition according to claim 1, wherein the at least one polymer capable of adhering to the keratinous fibers is present in an amount ranging from 0.1% to 50% by weight, relative to the total weight of the composition.

60. The composition according to claim 1, wherein the at least one polymer capable of adhering to the keratinous fibers is present in an amount ranging from 0.5% to 40% by weight by weight, relative to the total weight of the composition.

61. The composition according to claim 60, wherein the at least one polymer capable of adhering to the keratinous fibers is present in an amount ranging from 1% to 30% by weight by weight, relative to the total weight of the composition.

62. The composition according to claim 1, wherein the composition comprises an aqueous phase.

63. The composition according to claim 62, wherein the aqueous phase is chosen from water and a mixture of water and at least one water-miscible organic solvent.

64. The composition according to claim 63, wherein the at least one water-miscible organic solvent is chosen from lower monoalcohols having from 1 to 5 carbon atoms, glycols having from 2 to 8 carbon atoms, $C_3$–$C_4$ ketones, and $C_2$–$C_4$ aldehydes.

65. The composition according to claim 63, wherein the aqueous phase is present in an amount ranging from 0.1% to 98% by weight, relative to the total weight of the composition.

66. The composition according to claim 65, wherein the aqueous phase is present in an amount ranging from 1% to 80% by weight, relative to the total weight of the composition.

67. The composition according to claim 66, wherein the aqueous phase is present in an amount ranging from 5% to 65% by weight, relative to the total weight of the composition.

68. The composition according to claim 62, wherein the at least one polymer capable of adhering to the keratinous fibers is solubilized in the aqueous phase.

69. The composition according to claim 1, wherein the at least one polymer capable of adhering to the keratinous fibers is in the form of solid particles in aqueous dispersion.

70. The composition according to claim 1, further comprising at least one volatile oil.

71. The composition according to claim 70, wherein the at least one volatile oil is chosen from hydrocarbon oils, silicone oils, and fluorinated oils.

72. The composition according to claim 70, wherein the at least one volatile oil is present in an amount ranging from 0.1% to 98% by weight, relative to the total weight of the composition.

73. The composition according to claim 72, wherein the at least one volatile oil is present in an amount ranging from 1% to 65% by weight, relative to the total weight of the composition.

74. The composition according to claim 73, wherein the at least one volatile oil is present in an amount ranging from 5% to 65% by weight, relative to the total weight of the composition.

75. The composition according to claim 1, further comprising at least one nonvolatile oil.

76. The composition according to claim 75, wherein the at least one nonvolatile oil is present in an amount ranging from 0.1% to 50% by weight relative to the total weight of the composition.

77. The composition according to claim 76, wherein the at least one nonvolatile oil is present in an amount ranging from 0.1% to 30% by weight, relative to the total weight of the composition.

78. The composition according to claim 77, wherein the at least one nonvolatile oil is present in an amount ranging from 0.1% to 20% by weight, relative to the total weight of the composition.

79. The composition according to claim 1, wherein the at least one polymer capable of adhering to the keratinous fibers is solubilized or dispersed in the form of surface-stabilized particles in at least one liquid fatty phase.

80. The composition according to claim 1, further comprising at least one additional wax different from the at least one wax of the third solid particles.

81. The composition according to claim 80, wherein the at least one additional wax is present in an amount ranging from 0.1% to 35% by weight, relative to the total weight of the composition.

82. The composition according to claim 81, wherein the at least one additional wax is present in an amount ranging from 0.1% to 20% by weight, relative to the total weight of the composition.

83. The composition according to claim 82, wherein the at least one additional wax is present in an amount ranging from 1% to 10% by weight by weight, relative to the total weight of the composition.

84. The composition according to claim 80, wherein the at least one additional wax is in the form of particles having a mean size ranging from 50 nm to 50 μm.

85. The composition according to claim 84, wherein the at least one additional wax is in the form of particles having a mean size ranging from 50 nm to 10 μm.

86. The composition according to claim 1, further comprising at least one surfactant.

87. The composition according to claim 1, further comprising at least one additive chosen from colouring substances, antioxidants, fillers, preservatives, perfumes, neutralizing agents, thickeners, cosmetic active agents, sunscreens, coalescing agents, and plasticizers.

88. The composition according to claim 1, wherein the composition does not contain:
a) a mixture of 41% water, 10% isododecane, 5% ethanol, 4% hectorite, and 10% black iron oxide;
or
b) a mixture of 62.9% water, 10% stearic acid, 3% triethanolamine, 4% zinc oxide, and 10% black iron oxide,
wherein the percentages are expressed by weight relative to the total weight of the composition.

89. A mascara comprising a composition comprising, in a cosmetically acceptable medium comprising at least one volatile solvent, a nonvolatile fraction comprising:
a) at least one polymer capable of adhering to keratinous fibers,
b) main particles which are solid at 25° C. chosen from:
i) first solid particles comprising at least one first material chosen from crystalline and semicrystalline materials which are solid at 25° C. and have at least one of a first order phase transition, a melting transition and a combustion transition, greater than 100° C.,
ii) second solid particles comprising a second material chosen from at least one amorphous material having a glass transition temperature of greater than or equal to 60° C.,
iii) third solid particles comprising a third material chosen from at least one wax having a hardness of greater than or equal to 6.5 MPa, and
iv) mixtures thereof,
c) and optionally additional solid particles different from said main solid particles, the additional solid particles not being capable of coalescing at a temperature of less than or equal to 40° C.,
wherein the main solid particles and, where appropriate, the additional solid particles are present in the composition in an amount such that the volume fraction of the main solid particles and, where appropriate, of the additional solid particles is greater than or equal to 1% and less than 50% of the total volume of said nonvolatile fraction,
and, where appropriate, the volume fraction of the main solid particles is greater than or equal to 50% of the total volume of the main solid particles and of the additional solid particles.

90. A method of applying make-up to or for a nontherapeutic treatment of keratinous fibers, comprising:
applying to the keratinous fibers a composition comprising, in a cosmetically acceptable medium comprising at least one volatile solvent, a nonvolatile fraction comprising:
a) at least one polymer capable of adhering to the keratinous fibers,
b) main particles which are solid at 25° C. chosen from:
  i) first solid particles comprising at least one first material chosen from crystalline and semicrystalline materials which are solid at 25° C. and have at least one of a first order phase transition, a melting transition and a combustion transition, greater than 100° C.,
  ii) second solid particles comprising a second material chosen from at least one amorphous material having a glass transition temperature of greater than or equal to 60° C.,
  iii) third solid particles comprising a third material chosen from at least one wax having a hardness of greater than or equal to 6.5 MPa, and
  iv) mixtures thereof,
c) and optionally additional solid particles different from said main solid particles, the additional solid particles not being capable of coalescing at a temperature of less than or equal to 40° C.,
wherein the main solid particles and, where appropriate, the additional solid particles are present in the composition in an amount such that the volume fraction of the main solid particles and, where appropriate, of the additional solid particles is greater than or equal to 1% and less than 50% of the total volume of said nonvolatile fraction,
and, where appropriate, the volume fraction of the main solid particles is greater than or equal to 50% of the total volume of the main solid particles and of the additional solid particles.

91. The method according to claim 90, wherein the keratinous fibers are eyelashes.

92. A method for curling keratinous fibers, comprising:
applying to the keratinous fibers in an amount effective to curl the keratinous fibers, a composition comprising, in a cosmetically acceptable medium comprising at least one volatile solvent, a nonvolatile fraction comprising:
a) at least one polymer capable of adhering to the keratinous fibers,
b) main particles which are solid at 25° C. chosen from:
  i) first solid particles comprising at least one first material chosen from crystalline and semicrystalline materials which are solid at 25° C. and have at least one of a first order phase transition, a melting transition and a combustion transition, greater than 100° C.,
  ii) second solid particles comprising a second material chosen from at least one amorphous material having a glass transition temperature of greater than or equal to 60° C.,
  iii) third solid particles comprising a third material chosen from at least one wax having a hardness of greater than or equal to 6.5 MPa, and
  iv) mixtures thereof,
c) and optionally additional solid particles different from said main solid particles, the additional solid particles not being capable of coalescing at a temperature of less than or equal to 40° C.,
wherein the main solid particles and, where appropriate, the additional solid particles are present in the composition in an amount such that the volume fraction of the main solid particles and, where appropriate, of the additional solid particles is greater than or equal to 1% and less than 50% of the total volume of said nonvolatile fraction,
and, where appropriate, the volume fraction of the main solid particles is greater than or equal to 50% of the total volume of the main solid particles and of the additional solid particles.

93. The method according to claim 92, wherein the keratinous fibers are eyelashes.

94. A method for improving the curling capability of a composition for coating keratinous fibers, the composition comprising, in a cosmetically acceptable medium comprising at least one volatile solvent, a nonvolatile fraction comprising at least one polymer capable of adhering to the keratinous fibers, the method comprising:
adding main particles to the nonvolatile fraction, the particles being solid at 25° C. and chosen from:
  i) first solid particles comprising at least one first material chosen from crystalline and semicrystalline materials which are solid at 25° C. and have at least one of a first order phase transition, a melting transition and a combustion transition, greater than 100° C.,
  ii) second solid particles comprising a second material chosen from amorphous materials having a glass transition temperature of greater than or equal to 60° C.,
  iii) third solid particles comprising a third material chosen from at least one wax having a hardness of greater than or equal to 6.5 MPa, and
  iv) mixtures thereof,
wherein the non-volatile fraction optionally comprises additional solid particles different from said main solid particles, the additional solid particles not being capable of coalescing at a temperature of less than or equal to 40° C., the main solid particles and, where appropriate, the additional solid particles are present in the composition in an amount such that the volume fraction of the main solid particles and, where appropriate, the additional solid particles is greater than or equal to 1% and less than 50% of the total volume of the said nonvolatile fraction,
and, where appropriate, the volume fraction of the main solid particles is greater than or equal to 50% of the total volume of the main solid particles and of the additional solid particles.

95. The method according to claim 94, wherein the keratinous fibers are eyelashes.

96. The method according to claim 95, wherein the composition is present in a mascara.

97. A composition for coating keratinous fibers, comprising, in a cosmetically acceptable medium comprising at least one volatile solvent, a nonvolatile fraction comprising:
main particles which are solid at 25° C. chosen from:
  i) first solid particles comprising at least one first material chosen from crystalline and semicrystalline materials which are solid at 25° C. and have at least one of a first order phase transition, a melting transition and a combustion transition, greater than 100° C., ii) second solid particles comprising a second material chosen from at least one amorphous material having a glass transition temperature of greater than or equal to 60° C.,
iii) third solid particles comprising a third material chosen from at least one wax having a hardness of greater than or equal to 6.5 MPa, and
iv) mixtures thereof, c) and optionally additional solid particles different from said main solid particles, the additional solid particles not being capable of coalescing at a temperature of less than or equal to 40° C., wherein the main solid particles and, where appropriate, the additional solid particles are present in the composition in an amount such that the volume fraction of the main solid particles and, where appropriate, of the additional solid particles is greater than or equal to 1% and less than 50% of the total volume of said nonvolatile fraction, and, where appropriate, the volume fraction of the main solid particles is greater than or equal to 50% of the total volume of the main solid particles and of the additional solid particles, and wherein at least a portion of at least one of said main particles and said optional additional solid particles are chosen from at least one polymer capable of adhering to the keratinous fibers.

* * * * *

UNITED STATES PATENT AND TRADEMARK OFFICE
CERTIFICATE OF CORRECTION

| | |
|---|---|
| PATENT NO. | : 7,189,388 B2 |
| APPLICATION NO. | : 10/195432 |
| DATED | : March 13, 2007 |
| INVENTOR(S) | : Auguste et al. |

It is certified that error appears in the above-identified patent and that said Letters Patent is hereby corrected as shown below:

In claim 34, column 21, lines 4-5, "12 to MPa." should read --12 MPa.--.

In claim 60, column 22, lines 55-56, "by weight by weight, relative" should read --by weight, relative--.

In claim 61, column 22, lines 61-62, "by weight by weight, relative" should read --by weight, relative--.

In claim 83, column 24, line 7, "by weight by weight, relative" should read --by weight, relative--.

Signed and Sealed this

Twenty-sixth Day of June, 2007

JON W. DUDAS
*Director of the United States Patent and Trademark Office*